United States Patent
Lee et al.

(10) Patent No.: US 11,521,318 B2
(45) Date of Patent: Dec. 6, 2022

(54) METHOD, APPARATUS AND COMPUTER-READABLE MEDIUM FOR PROVIDING URINARY STONE INFORMATION

(71) Applicant: STARLABS Co., Seoul (KR)

(72) Inventors: Jun ho Lee, Seoul (KR); Min Soo Choo, Seoul (KR); Jin Kim, Seoul (KR); Chan Woo Kwak, Chuncheon-si (KR)

(73) Assignee: STARLABS Co., Seoul (KR)

( * ) Notice: Subject to any disclaimer, the term of this patent is extended or adjusted under 35 U.S.C. 154(b) by 219 days.

(21) Appl. No.: 16/952,442

(22) Filed: Nov. 19, 2020

(65) Prior Publication Data
US 2022/0067936 A1 Mar. 3, 2022

(30) Foreign Application Priority Data

Aug. 28, 2020 (KR) .................. 10-2020-0109211

(51) Int. Cl.
| | |
|---|---|
| *G06T 7/00* | (2017.01) |
| *G16H 50/50* | (2018.01) |
| *G16H 50/70* | (2018.01) |
| *G16H 50/20* | (2018.01) |
| *G16H 30/40* | (2018.01) |
| *G06N 3/04* | (2006.01) |
| *G06N 3/08* | (2006.01) |
| *G06T 19/20* | (2011.01) |
| *G16H 20/40* | (2018.01) |

(52) U.S. Cl.
CPC ......... *G06T 7/0014* (2013.01); *G06N 3/0454* (2013.01); *G06N 3/08* (2013.01); *G06T 19/20* (2013.01); *G16H 30/40* (2018.01); *G16H 50/20* (2018.01); *G16H 50/50* (2018.01); *G16H 50/70* (2018.01); *G06T 2207/10024* (2013.01); *G06T 2207/10072* (2013.01); *G06T 2207/30004* (2013.01); *G06T 2210/41* (2013.01); *G06T 2219/2016* (2013.01); *G16H 20/40* (2018.01)

(58) Field of Classification Search
CPC ....... G06T 7/0014; G06T 19/20; G16H 30/40; G06N 3/0454; G06N 3/08
See application file for complete search history.

(56) References Cited

FOREIGN PATENT DOCUMENTS

CN 111340130 A 6/2020

OTHER PUBLICATIONS

Min Soo Choo et al.;A Prediction Model Using Machine Learning Algorithm for Assessing Stone-Free Status after Single Session Shock Wave Lithotripsy to Treat Ureteral Stones; The Journal of Urology; Dec. 2018;1371-1377(pages); vol. 200; American Urological Association Education and Research, Inc.; U.S.A.

*Primary Examiner* — Edward Park

(57) ABSTRACT

The present invention relates to a method for providing urinary stone information, and more particularly, to a method for providing urinary stone information, capable of providing information necessary for urinary stone surgery by detecting a region where a stone is present from a plurality of tomography images by using a machine learning model, and automatically extracting information including a location and a size of the stone.

10 Claims, 14 Drawing Sheets

METHOD, APPARATUS AND COMPUTER-READABLE MEDIUM FOR PROVIDING URINARY STONE INFORMATION

BACKGROUND OF THE INVENTION

1. Field of the Invention

The present invention relates to a method for providing urinary stone information, and more particularly, to a method for providing urinary stone information, capable of providing information necessary for urinary stone surgery by detecting a region where a stone is present from a plurality of tomography images by using a machine learning model, and automatically extracting information including a location and a size of the stone.

2. Description of the Related Art

A urinary tract refers to a path through which urine is discharged from a body after being produced, and a urinary stone refers to a stone formed in a passage through which the urine is transported and excreted after being produced. The stone may be formed anywhere in the urinary tract, and may vary in size and number from one to several. Urological stones are broadly classified into kidney stones, ureteral stones, and bladder stones. In actual clinical practice, the bladder stones are very rare, whereas there is a high proportion of the ureteral stone. The number of urinary stone patients was 280,000 in 2013, showing an annual average increase of 2.8%, and the urinary stone is a disease that frequently occurs mainly in active 20s to 40s and occurs more than twice as many in men than in women with a relapse probability of 70% or more. In addition, treatment expenses were 192.6 billion KRW in 2013, showing an annual average increase of 6%. Symptoms may include hematuria and a severe pain in the side.

Since the urinary stone is a crystal formed of various substances, the urinary stone has a very sharp shape as shown in FIG. 1, which leads to an extreme pain as if a knife is stabbed into a body. In some cases, a patient is required to be treated with a pain reliever injection to move because the patient may feel breathless due to an acute pain. Therefore, when symptoms due to the urinary stone appear, a prompt treatment is required.

A treatment scheme of the urinary stone varies depending on a patient, in which the treatment scheme is selected according to symptoms, a size of the stone, the presence or stone of urinary retention or urinary tract infection, the presence or stone of anatomical abnormalities in the urinary tract, a cause of the stone, and the like.

When the size of the stone is less than 5 mm, a patient is required to drink a large amount of water, take a pain reliever, perform exercises such as jump rope, and be regularly subject to radiography while waiting for natural discharge of the stone. However, urinary diversion surgery has to be performed emergently in a case of fever or severe symptoms such as nausea and vomiting, caused by urinary tract obstruction due to the urinary stone and urinary tract infection accompanied thereby, or in a case of a urinary stone when a patient has one kidney.

When it is difficult to naturally discharge the stone, extracorporeal shock wave lithotripsy, ureteroscopic removal of stone, or laparoscopic surgery/laparotomy may be performed.

The extracorporeal shock wave lithotripsy is a treatment scheme of inducing the natural discharge of the stone by crushing the stone with shock waves from an outside of the body, and the ureteroscopic removal of stone is a surgical scheme of inserting an endoscope through a urethra, crushing the stone, and removing the stone. When the urinary stone is too large to be resolved with the extracorporeal shock wave lithotripsy or the ureteroscopic removal of stone, the urinary stone has to be removed through the laparoscopic surgery or the laparotomy. However, the laparoscopic surgery or the laparotomy has not been frequently performed in recent years.

The extracorporeal shock wave lithotripsy is a scheme of crushing and discharging the stone with only external shock waves without invading the body, and is widely used because the extracorporeal shock wave lithotripsy does not require anesthesia, does not cause pain, and does not require skin incisions or the like. However, for the extracorporeal shock wave lithotripsy, it is necessary to recognize an accurate location and an accurate size of the urinary stone in order to crush the urinary stone with ultrasonic waves. Although the location and the size may be recognized through X-ray radiography, it is preferable to recognize the location and the size through computed tomography (CT) in order to obtain accurate urinary stone information.

Conventionally, doctors have been manually checking tomography images of a urinary stone patient with naked eyes to find a urinary stone, and measuring a found urinary stone image by using a ruler or the like so as to determine an approximate size of the urinary stone. However, such a scheme has a problem that it takes a long time to find the urinary stone from the tomography image, and since measurement accuracy is low, it is difficult to select an appropriate treatment scheme and proceed with the treatment. Therefore, there is a demand for developing a method for analyzing a tomography image to provide information that may assist with a treatment of a urinary stone.

SUMMARY OF THE INVENTION

An object of the present invention is to provide a method for providing urinary stone information, capable of providing information necessary for urinary stone surgery by detecting a region where a stone is present from a plurality of tomography images by using a machine learning model, and automatically extracting information including a location and a size of the stone.

To achieve the above objects, according to the present invention, there is provided a method for providing urinary stone information, which is performed in a computing system having at least one processor and at least one memory, the method including: extracting at least one stone region information by using a first machine learning model trained for each of a plurality of tomography images having mutually different tomography heights; extracting image-specific stone detail information related to a region actually corresponding to a stone in each stone region based on color information of a pixel in the stone region of the tomography image corresponding to the at least one stone region information; clustering the image-specific stone detail information for a same stone among the image-specific stone detail information of each of the tomography images; extracting stone-specific detail information including a size of each stone based on information including the stone region information and the image-specific stone detail information; and generating or providing the urinary stone information based on at least one of the tomography image, the stone region information, the image-specific stone detail information, and the stone-specific detail information according to a request of a user.

In the present invention, in the extracting of the image-specific stone detail information, a pixel having color information corresponding to a preset RGB value range among pixels in the stone region of the tomography image may be determined as the region actually corresponding to the stone.

In the present invention, the tomography heights may be set with a preset interval, and in the extracting of the stone-specific detail information, a volume of each stone may be extracted based on an area of the image-specific stone detail information and the interval of the tomography heights.

In the present invention, the volume of the stone may be extracted by cumulatively summing a value obtained by multiplying the interval of the tomography heights by an average of areas of the image-specific stone detail information of two tomography images taken at adjacent tomography heights among the tomography images including the image-specific stone detail information for the stone.

In the present invention, the clustering of the image-specific stone detail information may include: arranging the tomography images according to the tomography heights; extracting coordinates of the image-specific stone detail information of the arranged tomography image; and determining whether the image-specific stone detail information is for the same stone by comparing the coordinates extracted from the image-specific stone detail information of the arranged tomography image with coordinates of an adjacent tomography image.

In the present invention, the stone-specific detail information may include coordinates of the stone, a maximum sectional area of the stone, a volume of the stone, and a length of a major axis of the stone.

In the present invention, the method for providing the urinary stone information may further include displaying the urinary stone information generated according to the request of the user, wherein, in the displaying of the urinary stone information, the extracted urinary stone information may be displayed by overlaying the extracted urinary stone information on a three-dimensional (3D) body model generated based on the tomography images.

In the present invention, in the displaying of the urinary stone information, a display angle and a size of the 3D body model may be adjustable according to an input of the user.

In the present invention, the method for providing the urinary stone information may further include extracting a success probability of surgery by using a preset condition or a second machine learning model trained based on information including the stone region information and the image-specific stone detail information for each stone.

In the present invention, the first machine learning model may extract the stone region information based on a you-only-look-once (YOLO) artificial neural network algorithm.

To achieve the above objects, according to the present invention, there is provided an apparatus for providing urinary stone information, the apparatus including: a stone region information extraction unit for extracting at least one stone region information by using a first machine learning model trained for each of a plurality of tomography images having mutually different tomography heights; an image-specific stone detail information extraction unit for extracting image-specific stone detail information related to a region actually corresponding to a stone in each stone region based on color information of a pixel in the stone region of the tomography image corresponding to the at least one stone region information; an image-specific stone detail information clustering unit for clustering the image-specific stone detail information for a same stone among the image-specific stone detail information of each of the tomography images; a stone-specific detail information extraction unit for extracting stone-specific detail information including a size of each stone based on information including the stone region information and the image-specific stone detail information; and a urinary stone information generation unit for generating or providing the urinary stone information based on at least one of the tomography image, the stone region information, the image-specific stone detail information, and the stone-specific detail information according to a request of a user.

To achieve the above objects, according to the present invention, there is provided a computer-readable medium recorded with a program for performing the method for providing the urinary stone information as described above.

According to one embodiment of the present invention, a urinary stone can be automatically detected from a tomography image by using a machine learning model.

According to one embodiment of the present invention, the urinary stone can be detected very rapidly by detecting the urinary stone based on a YOLO artificial neural network algorithm.

According to one embodiment of the present invention, information including a size and a location of the detected urinary stone can be automatically extracted.

According to one embodiment of the present invention, a volume of the urinary stone can be extracted based on an area of the urinary stone in the tomography image.

According to one embodiment of the present invention, an appropriate treatment scheme can be selected by extracting a success probability of urinary stone surgery by using the machine learning model.

According to one embodiment of the present invention, urinary stone information can be clearly recognized by displaying the urinary stone information on a 3D body model.

DETAILED DESCRIPTION OF THE INVENTION

Figure 1:
FIG. 1 is a view showing a shape of a urinary stone.

In the following, various embodiments and/or aspects are disclosed with reference to the drawings. In the following description, for the purpose of explanation, a plurality of specific details are disclosed in order to assist in an overall understanding of one or more aspects. However, it will be appreciated by a person having ordinary skill in the art to which the invention pertains that the aspect(s) may be practiced without the specific details. The following description and the accompanying drawings will set forth certain illustrative aspects of the one or more aspects in detail. However, the aspects are provided for illustrative purposes, some of various schemes based on principles of various aspects may be used, and descriptions are intended to include all the aspects and equivalents thereof.

In addition, various aspects and features will be proposed by a system that may include a plurality of devices, components, and/or modules. It will also be understood and appreciated that various systems may include additional devices, components, and/or modules, and/or that various systems may not include all of the devices, components, modules, and the like discussed in association with the drawings.

In the present disclosure, "embodiment", "example", "aspect", "illustration", and the like may not be construed as having any disclosed aspect or design that is better or advantageous than other aspects or designs. Each of the terms "unit", "component", "module", "system", "interface", and the like used below generally refers to a computer-related entity, and may refer to, for example, hardware, a combination of hardware and software, or software.

In addition, it will be understood that the terms "comprises" and/or "comprising" indicate the presence of corresponding features and/or elements, but do not exclude the presence or addition of one or more other features, components, and/or groups thereof.

Further, although any of the terms including ordinal numbers such as "first" and "second" may be used to describe various elements, the elements are not limited by the terms. The terms are only used to distinguish one element from another element. For example, without departing from the scope of the present invention, a first element may be termed as a second element, and, similarly, the second element may be termed as the first element. The term "and/or" includes any combination of a plurality of disclosed items related thereto, or one of the disclosed items related thereto.

In addition, in embodiments of the present invention, unless separately defined otherwise, all terms used herein, including technical terms and scientific terms, have the same meaning as how they are generally understood by the person having ordinary skill in the art to which the invention pertains. Any term defined in a general dictionary shall be construed to have a meaning corresponding to the meaning in the context of the relevant art, and shall not be construed to have an idealistic or excessively formalistic meaning unless explicitly defined otherwise in the embodiments of the present invention.

In the present disclosure, the term "urinary stone" refers to a stone formed in a passage in which urine is transported, stored, and excreted after being produced, and the term "urinary stone" is a concept that includes a kidney stone, a renal pelvic stone, a ureteral stone, a bladder stone, and a urethral stone.

Figure 2:
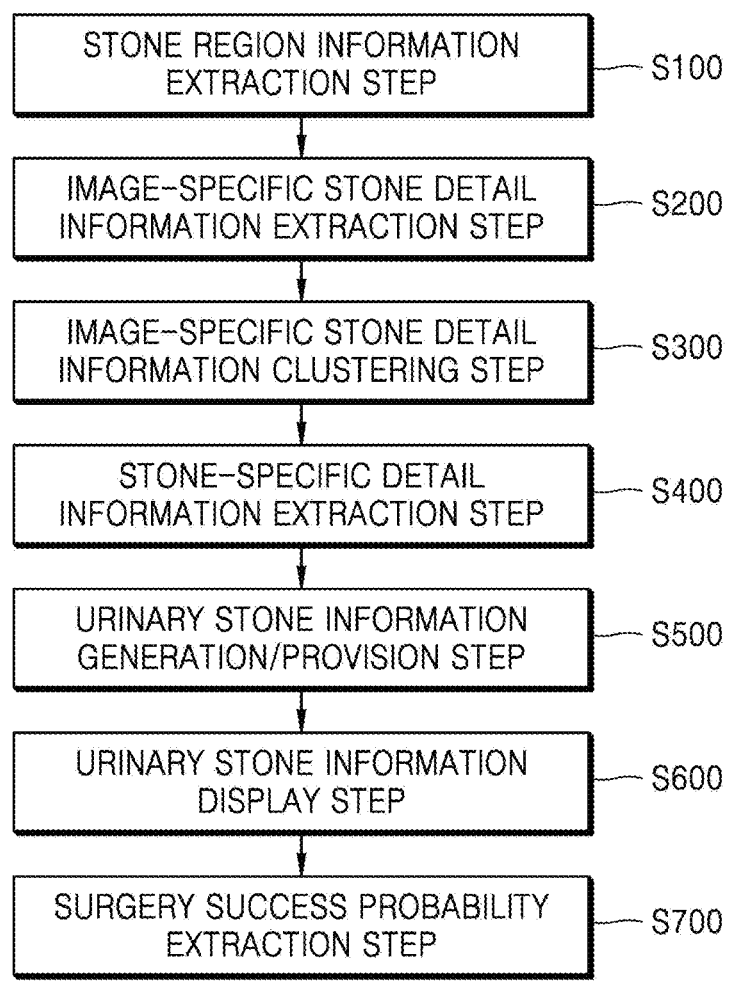
FIG. 2 is a view schematically showing each step of a method for providing urinary stone information according to one embodiment of the present invention.

FIG. 2 is a view schematically showing each step of a method for providing urinary stone information according to one embodiment of the present invention.

Referring to FIG. 2, according to one embodiment of the present invention, a method for providing urinary stone information may include: extracting at least one stone region information by using a first machine learning model trained for each of a plurality of tomography images having mutually different tomography heights (S100); extracting image-specific stone detail information related to a region actually corresponding to a stone in each stone region based on color information of a pixel in the stone region of the tomography image corresponding to the at least one stone region information (S200); clustering the image-specific stone detail information for a same stone among the image-specific stone detail information of each of the tomography images (S300); extracting stone-specific detail information including a size of each stone based on information including the stone region information and the image-specific stone detail information (S400); generating or providing the urinary stone information based on at least one of the tomography image, the stone region information, the image-specific stone detail information, and the stone-specific detail information according to a request of a user (S500); displaying the urinary stone information generated according to the request of the user (S600); and extracting a success probability of surgery by using a preset condition or a second machine learning model trained based on information including the stone region information and the image-specific stone detail information for each stone (S700).

In the present invention, through a series of steps as described above, the stone region information may be extracted by detecting the stone region where the stone is present from the tomography images, the image-specific stone detail information for the region where the stone is actually present in the stone region may be extracted, and the stone-specific detail information on the stone may be extracted by clustering the image-specific stone detail information for each stone, so that the urinary stone information may be provided to a medical staff. In addition, the urinary stone information may be displayed so that the medical staff may easily recognize the urinary stone information, and the success probability of the surgery for the urinary stone may be automatically extracted and provided to assist the medical staff in selecting a treatment scheme.

First, in the step S100 of extracting the stone region information, the stone may be detected from the tomography images by using the trained first machine learning model to detect the stone region that is a region including the stone, and the stone region information on the stone region may be extracted. In the present invention, since the stone is detected through the first machine learning model as described above, a conventional process of finding the urinary stone while manually checking the tomography images by the medical staff may be automated, and the urinary stone may be detected with high accuracy.

Then, in the step S200 of extracting the image-specific stone detail information, the region actually corresponding to the stone may be determined in the extracted stone region to extract the image-specific stone detail information. The first machine learning model may extract the stone region that is the region including the stone, in which the stone region is a region that includes the urinary stone, including a region (pixel) in which the urinary stone is actually photographed and a region (pixel) that is not the urinary stone. Therefore, accurate information on the stone may be recognized by separating and detecting the region actually corresponding to the stone, and a section of the stone may be recognized in a corresponding tomography image by separating the region corresponding to the stone as described above, so that the section of the stone may be used to extract the urinary stone information such as an area of the section and a volume of the urinary stone.

Thereafter, in the step S300 of clustering the image-specific stone detail information, the image-specific stone detail information for the same stone among the image-specific stone detail information of each of the tomography images may be clustered. As described above, since the image-specific stone detail information for the same stone is collected and organized, detailed information on a corresponding urinary stone may be recognized.

Then, in the step S400 of extracting the stone-specific detail information, the stone-specific detail information may be extracted based on the clustered image-specific stone detail information. The stone-specific detail information may include information such as coordinates, a volume, a sectional area, and a length of the stone.

Thereafter, in the step S500 of generating or providing the urinary stone information, necessary information may be extracted from the tomography image, the stone region information, the image-specific stone detail information, and the stone-specific detail information according to the request of the user to generate the urinary stone information or provide the urinary stone information to the user.

Then, in the step S600 of displaying the urinary stone information, the urinary stone information may be displayed. In one embodiment of the present invention, the urinary stone information may be displayed on a three-dimensional (3D) body model generated based on the tomography images, so that the user may recognize the urinary stone information at a glance.

Thereafter, in the step S700 of extracting the success probability of the surgery, the success probability of the surgery for each stone, especially extracorporeal shock wave lithotripsy, may be extracted by using the trained second machine learning model or the preset condition. In the present invention, the success probability of the extracorporeal shock wave lithotripsy for the stone may be extracted according to the preset condition, for example, the location of the stone and the size of the stone, or the success probability of the extracorporeal shock wave lithotripsy may be extracted based on the trained second machine learning model. In the second machine learning model, success or failure of surgery of an existing patient may be labeled on a tomography image in which a urinary stone of the existing patient is photographed, and may be used as learning data, so that a success probability of surgery for determining whether a urinary stone in a newly input tomography image is suitable for the surgery may be extracted. As described above, in the present invention, since the success probability of the surgery is extracted and provided, it is possible to assist the medical staff who is the user in deciding whether to attempt the surgery (extracorporeal shock wave lithotripsy) or other treatment schemes.

Figure 3:
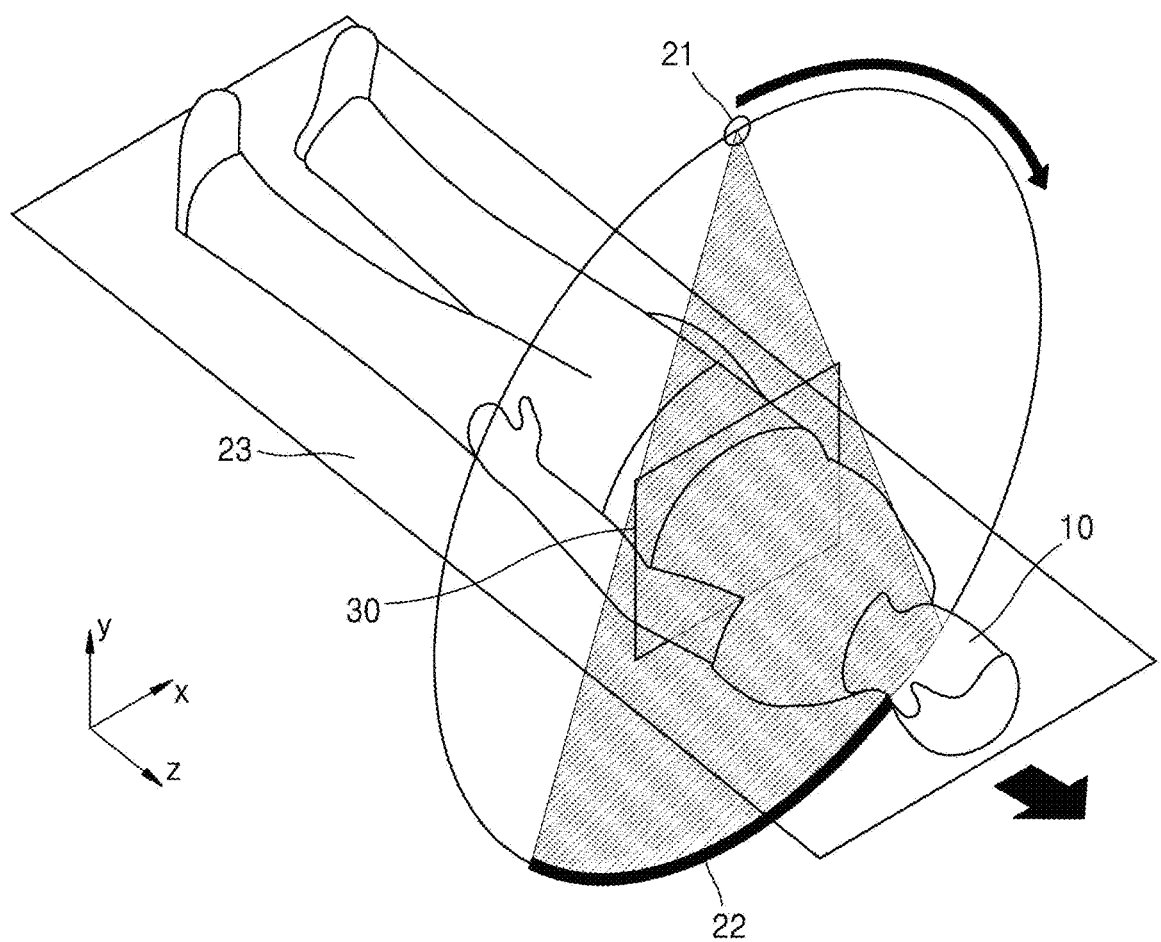
FIG. 3 is a view schematically showing a state of taking a tomography image.

FIG. 3 is a view schematically showing a state of taking a tomography image.

Referring to FIG. 3, in order to obtain the tomography images used in the present invention, a device for taking a tomography image is shown in the drawing. As shown in FIG. 3, when a photographing target patient 10 is lying on a platform 23 provided in the device, an X-ray may be irradiated toward the patient 10 from an X-ray light source 21 of the device, and a sensor 22 located on an opposite side of the X-ray light source 21 may detect the X-ray transmitted through the patient 10. In this case, while the X-ray light source 21 and the sensor 22 rotate on an XY-plane as shown in FIG. 3, the X-ray may be irradiated to the patient 10 in various directions, and the transmitted X-ray may be detected.

When the X-ray is irradiated to the patient 10, a part of the X-ray may be absorbed by a body of the patient 10, and a part of the X-ray may pass through the patient 10 to reach the sensor 22. The sensor 22 may detect an amount of the transmitted X-ray. As described above, the amount of the transmitted X-ray may vary depending on a transmittance, a thickness, and the like of each organ inside the body of the patient 10.

As described above, a sinogram may be obtained by detecting the transmitted X-ray according to an irradiation angle of the X-ray. The sinogram is a visualization of the amount of the transmitted X-ray detected by the sensor 22 according to an angle by using a gray scale. In other words, the sinogram may refer to a graph obtained by acquiring X-ray photographs at various angles. In general, more X-rays may be absorbed as the color becomes closer to white. In this case, it may be determined that a large amount of X-ray is absorbed because a body organ at a corresponding location has a high absorptance or a large size (thickness).

Although the sinogram displays an amount of an absorbed X-ray, a sectional shape of the body may not be immediately recognized through the sinogram. Therefore, it is necessary to process the sinogram to convert the sinogram into a form that is readable by a human.

Meanwhile, the sinogram as described above may express an amount of an X-ray transmitted through an object as a curvilinear integral of an absorption amount in a corresponding X-ray trajectory. In addition, since the light source and the sensor rotate, a rotation variable has to be added to a curvilinear integral function. Such a function is referred to as "Radon transform". In other words, the sinogram is a result of physically performing the Radon transform on a photographed section of the patient 10, and inverse Radon transform may be performed in order to obtain the photographed section from the sinogram. In other words, a tomography image 30 of the body of the patient 10 through which the X-ray is transmitted may be obtained by performing the inverse Radon transform on the sinogram obtained through the sensor 22.

After the tomography image of the body is obtained as described above, the platform 23 may move in a Z-direction, and subsequently, another tomography image may be obtained by irradiating and detecting the X-ray while rotating the light source 21 and the sensor 22. In other words, a plurality of tomography images having mutually different tomography heights (Z-axis coordinates) may be obtained while moving the platform 23 in the Z-direction, that is, a height direction of the patient 10 through the device shown in FIG. 3. Preferably, the tomography height may be set with the same preset interval.

Figure 4:
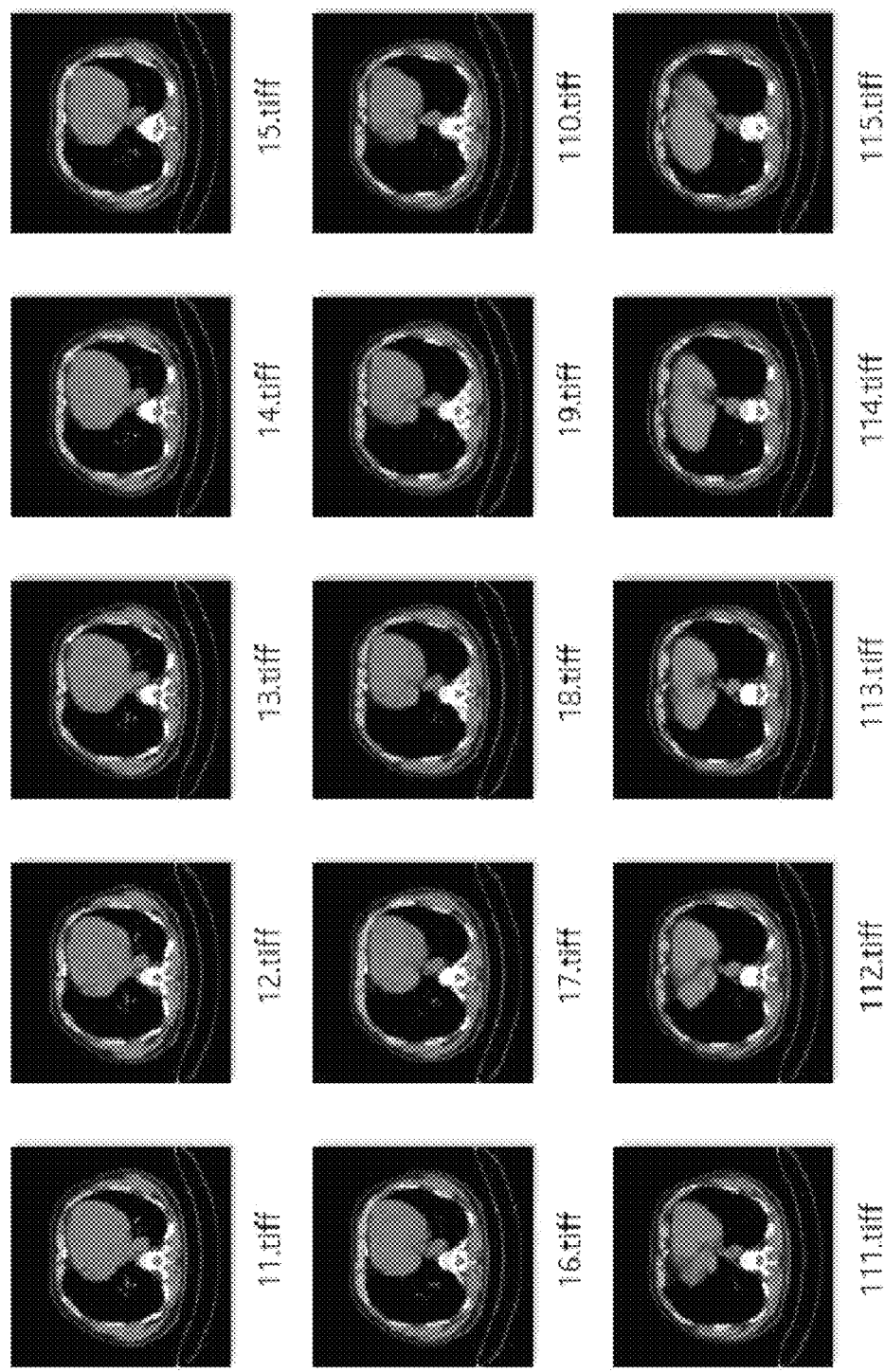
FIG. 4 is a view schematically showing a plurality of tomography images for extracting the urinary stone information according to one embodiment of the present invention.

FIG. 4 is a view schematically showing a plurality of tomography images for extracting the urinary stone information according to one embodiment of the present invention.

Referring to FIG. 4, it may be found that the tomography images taken as shown in FIG. 3 are stored. The tomography images taken as described above may be arranged and stored in an order according to the tomography heights. In the present invention, the urinary stone information may be extracted by detecting and analyzing the urinary stone based on the tomography images.

Figure 5:
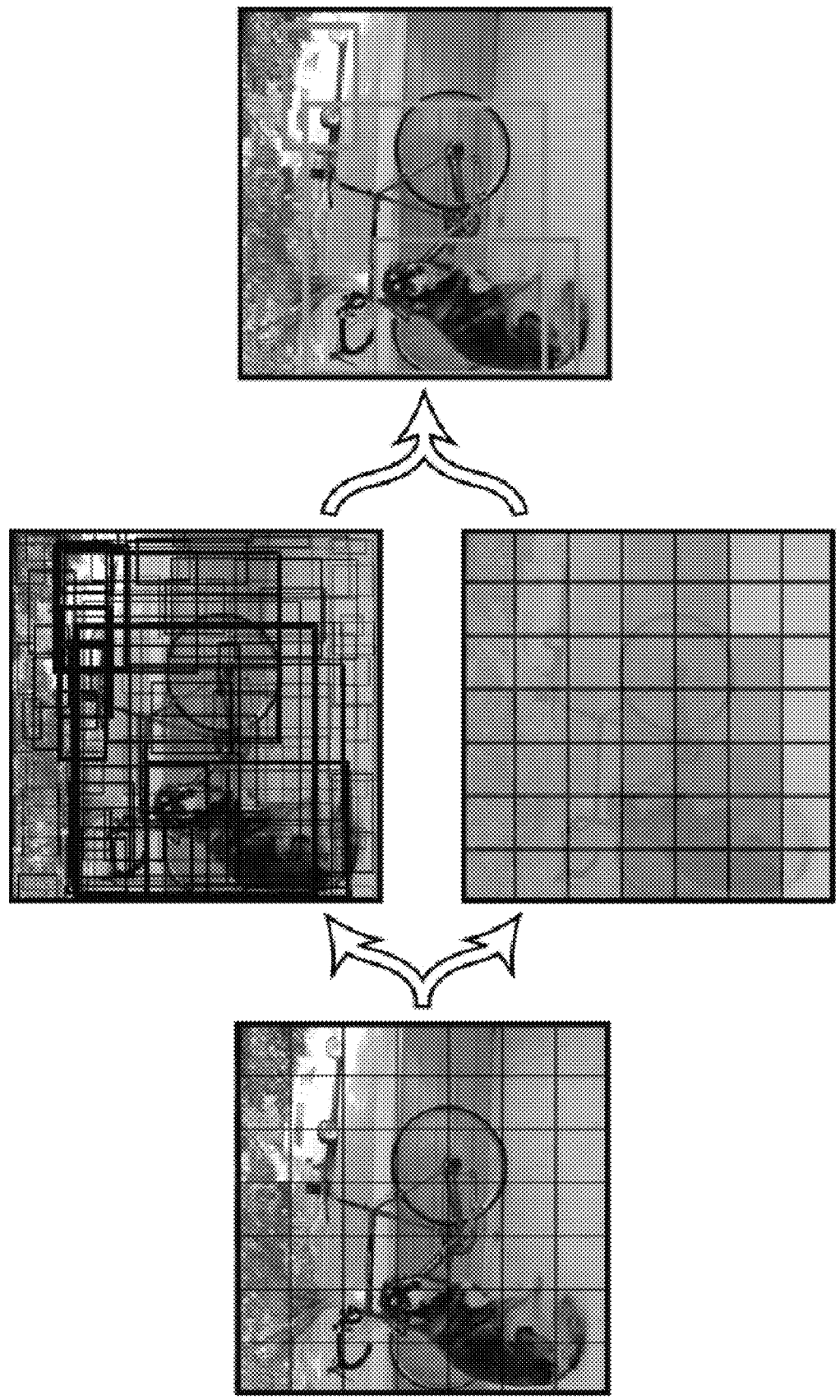
FIG. 5 is a view schematically showing a process of detecting a region where a stone is present by a first machine learning model according to one embodiment of the present invention.

FIG. 5 is a view schematically showing a process of detecting a region where a stone is present by a first machine learning model according to one embodiment of the present invention.

In one embodiment of the present invention, the stone region information on the region where the stone is present may be extracted through the first machine learning model. The first machine learning model may have the same structure as an artificial neural network, and the stone region information on the region where the stone is present may be extracted through learning of the artificial neural network.

In one embodiment of the present invention, the first machine learning model may extract the stone region information based on a you-only-look-once (YOLO) artificial neural network algorithm.

A plurality of artificial neural networks for checking whether a specific object is included in an image and extracting an object region from the image have been developed.

In general, since an object may be distributed in various regions in the image, it is necessary to check a range within which the object is present through a bounding box before extracting the object from the image. There are several algorithms for predicting such a bounding box.

In a sliding window scheme, a sliding window region image in an image may be transmitted to an object class prediction function. In the sliding window scheme, in order to search for an object in an image, a process of generating a bounding box having a predetermined size from an upper left end of an image and searching for an object in the bounding box may be repeatedly performed.

Meanwhile, objects may have various sizes. In order to normalize the image in the bounding box to a specific size that allows the object to be recognizable, an image pyramid is generally generated. The image may be downsampled until the image reaches a minimum size. Object detection may be performed for each of the downsampled images. In general, the pyramid has a maximum of 64 levels.

Object classification may be performed with very high accuracy in an artificial neural network such as a convolutional neural network (CNN). However, it is impossible to perform CNN object classification on a plurality of window images obtained from a sliding window as described above. Therefore, the above problem has been solved through a region-based CNN (regions with CNN; R-CNN) algorithm that considers regions. In an R-CNN, the CNN has been applied by reducing the number of bounding boxes required for the object classification. However, the R-CNN also has a problem that it takes a long time to process the CNN for a plurality of regions.

Therefore, neural networks such as a spatial pyramid pooling network (SPP-net) for calculating the CNN for an entire image only once in order to reduce the time required and a fast R-CNN for calculating a gradient through spatial pooling have been developed, so that a faster calculation speed has been achieved as compared with previous neural networks. However, the neural networks still have not reached a speed enough to perform real-time processing on a video.

The you-only-look-once (YOLO) artificial neural network algorithm refers to an artificial neural network in which a processing speed of such an object detection neural network is dramatically improved. The YOLO artificial neural network algorithm may simultaneously perform detection of a location of a bounding box and classification of a class of an object at a final output end of a network. With only a single network, a feature may be extracted, a bounding box may be generated, and a class may be classified at once. Therefore, a structure of the network may be very simple, and the network may achieve a high speed.

Referring to FIG. 5, when an input image on a left side of the drawing passes through a YOLO artificial neural network, two pieces of data as shown in a middle of the drawing may be obtained. The two pieces of data may be final outputs of the artificial neural network. In such outputs, information on a class present in a corresponding grid cell when a plurality of bounding boxes and an image are divided into S×S grids may be encoded. An image on a right side of the drawing may be generated by using the final outputs of the network, so the network may not directly generate the image on the right side.

An image at a top center of the drawing shows information on the bounding boxes. The bounding boxes having mutually different sizes are shown in the drawing. The network may divide the image into S×S grids. In an embodiment of FIG. 5, the image was divided into 7×7 grids. In each grid, two bounding boxes, each having a center located inside the grid and a size that is not uniform, may be generated. Since there are 7×7=49 grid cells, a total of 98 bounding boxes may be generated.

Among the bounding boxes, a bounding box within which an object is confidently determined to be present may be displayed in bold. This may indicate a case where a confidence score is greater than or equal to a preset value when the confidence score is extracted. The remaining bounding boxes except for bounding boxes having a confidence score that is greater than or equal to the preset value may be deleted. When the remaining bounding boxes are sorted out, three bounding boxes may be left as shown in the image on the right side of the drawing.

Meanwhile, a color of the bounding box may represent a class of the object. An image at a bottom center of the drawing was divided into 7×7 grids to have a total of 49 grid cells. Each grid cell may express the class of the object within a bounding box proposed in a corresponding region with colors.

Therefore, when the above contents are collectively considered, finally, the class of the object inside the three bounding boxes may be found. Accordingly, a final result as shown in the image on the right side of the drawing may be obtained.

Figure 6:
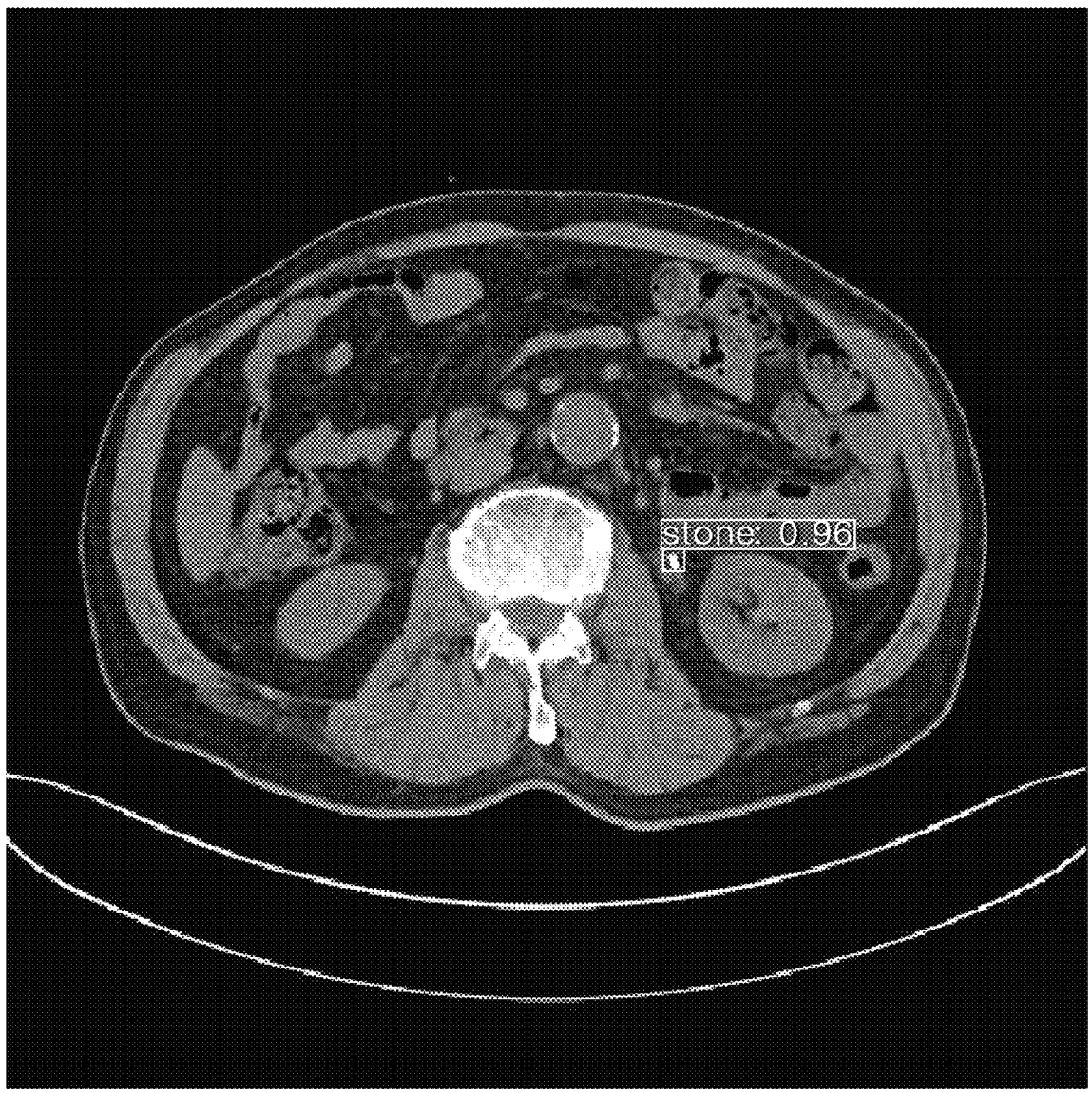
FIG. 6 is a view schematically showing a state in which stone region information is extracted from the tomography image by the first machine learning model according to one embodiment of the present invention.

When the YOLO artificial neural network is used as the first machine learning model of the present invention, a urinary stone, which is an object, may be detected from an input tomography image to extract the stone region information including the urinary stone. The stone region information extracted as described above is shown in FIG. 6. In FIG. 6, a region determined to include the urinary stone is indicated by a red rectangle in the tomography image, and a label "stone" is attached to the region.

The YOLO artificial neural network may increase accuracy of extraction of the confidence score and accuracy of generation of the boundary box through learning. The learning may be performed by inputting a tomography image including a urinary stone of a urinary stone patient. In one embodiment of the present invention, the region including the urinary stone in the tomography image including the urinary stone may be labeled and input, so that the YOLO artificial neural network may be trained through a supervised learning scheme. The YOLO artificial neural network may detect the urinary stone with higher accuracy as the number of tomography images used to perform the learning increases.

Meanwhile, in one embodiment of the present invention, the success probability of the surgery may be extracted by using the second machine learning model. The second machine learning model may extract the success probability of the surgery based on information including the image-specific stone detail information extracted from the tomography image. The second machine learning model may also be implemented through an artificial neural network model, and, similar to the first machine learning model, accuracy of the extracted success probability of the surgery may be increased through the learning. The learning may also be performed by inputting the tomography image including the urinary stone of the urinary stone patient. In one embodiment of the present invention, a post-operative course of the patient in the tomography image including the urinary stone may be labeled and input in the image, so that the second machine learning model may be trained through the supervised learning scheme.

Figure 7:
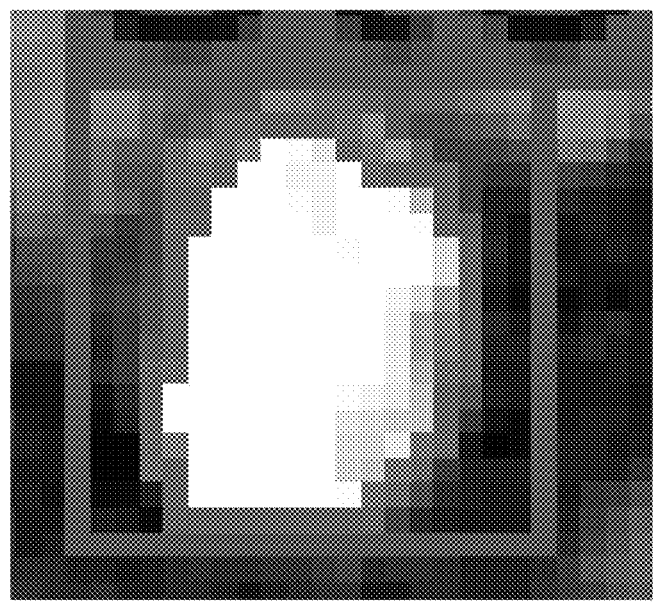
FIG. 7 is a photograph visually displaying a surface area of the stone according to one embodiment of the present invention.

FIG. 7 is a photograph visually displaying a surface area of the stone according to one embodiment of the present invention.

In one embodiment of the present invention, in the step S200 of extracting the image-specific stone detail information, a pixel having color information corresponding to a preset RGB value range among pixels in the stone region of the tomography image may be determined as the region actually corresponding to the stone.

As described above, the stone region extracted in the step S100 of extracting the stone region information refers to a region where a stone is determined to be present in the tomography image. In one embodiment of the present invention, the stone region may be extracted in a rectangular shape including the stone in the tomography image, and it is necessary to distinguish between a region where the stone is actually present and a region where the stone is absent in the stone region.

In one embodiment of the present invention, the pixel having the color information corresponding to the preset RGB value range in the stone region may be determined as the region actually corresponding to the stone to distinguish between the region where the stone is present and the region where the stone is absent.

In one embodiment of the present invention, the tomography image refers to an image obtained by measuring the X-ray transmitted through the body of the patient, in which a region where a large amount of X-ray is absorbed may be displayed as being close to white, and a region where almost no X-ray is absorbed may be displayed as being close to black. In a case of the urinary stone, a large amount of X-ray may be absorbed, so that the urinary stone may be displayed as being close to white in the tomography image. Preferably, a pixel in which each of R, G, and B is greater than or equal to 210 in a 24-bit RGB color may be determined as the region actually corresponding to the stone. In FIG. 7, a region obtained by extracting the region actually corresponding to the stone from the stone region indicated by a rectangle according to the criterion as described above is displayed in red.

In the present invention, since the region actually corresponding to the stone is extracted as described above, information on the stone, such as an area of the stone and a location of the stone in the tomography image, may be recognized and provided to the medical staff to assist with the treatment.

Meanwhile, the present invention has a double configuration of extracting the stone region through the first machine learning model and determining the region actually corresponding to the stone based on the color information of the pixel. As described above, in the present invention, since a machine learning model using the artificial neural network and a rule-based model based on the color information share roles to detect the stone region and extract the region corresponding to the stone, the stone may be detected at a high speed with increased accuracy. In one embodiment of the present invention, since the stone region is extracted through the first machine learning model, the stone may be detected with high accuracy from the tomography images. In this case, since the first machine learning model extracts only the stone region including the stone, an amount of computation may be reduced, which enables the detection at a high speed. Meanwhile, since the region actually corresponding to the stone is extracted from the stone region through the rule-based model having a simple logic, the region actually corresponding to the stone may be extracted from the stone region at a very high speed.

Figure 8:
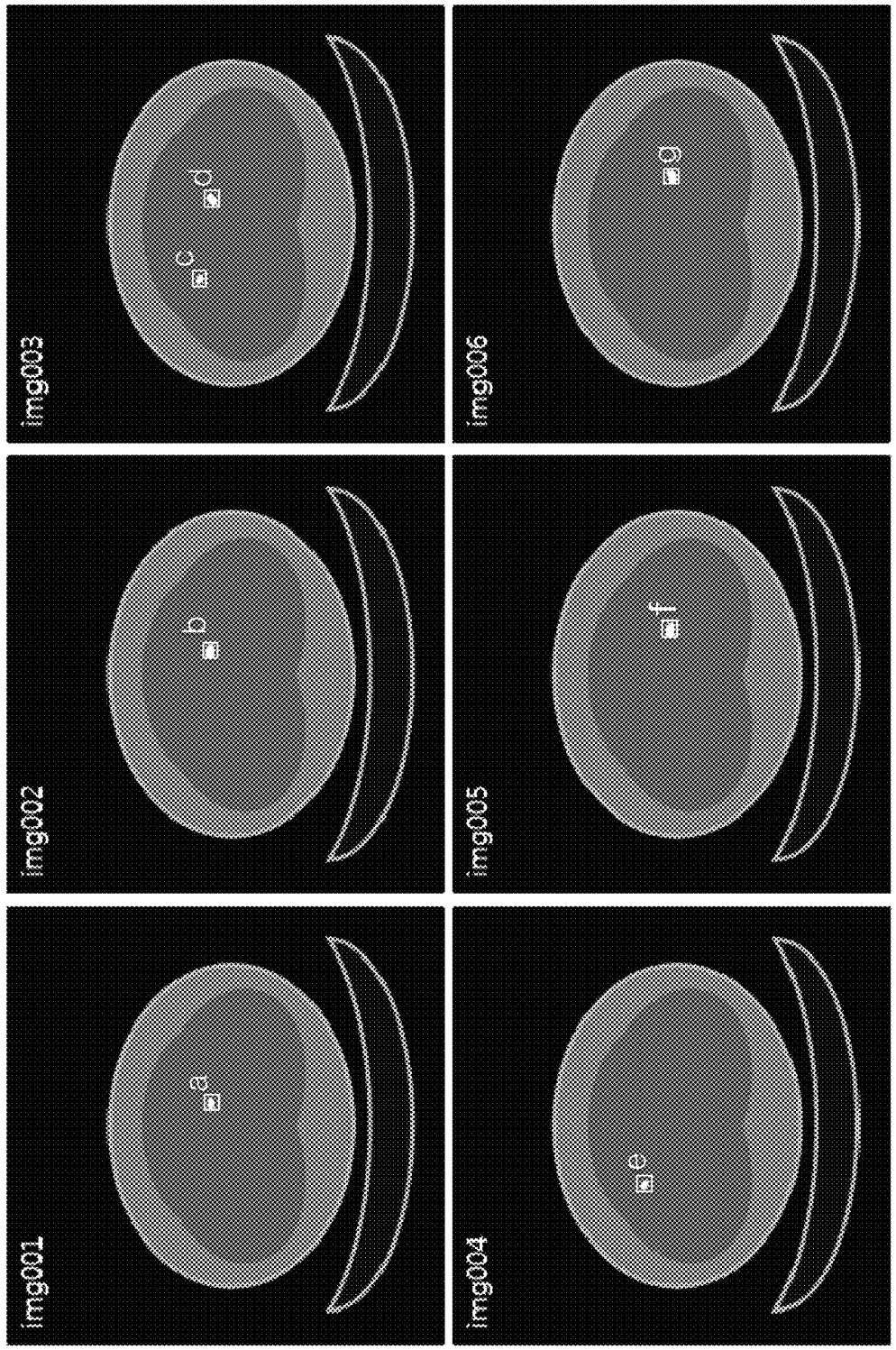
FIG. 8 is a view schematically showing a process of clustering image-specific stone detail information of the tomography images according to one embodiment of the present invention.

FIG. 8 is a view schematically showing a process of clustering image-specific stone detail information of the tomography images according to one embodiment of the present invention.

In one embodiment of the present invention, the step S300 of clustering the image-specific stone detail information may include: arranging the tomography images according to the tomography heights (S310); extracting coordinates of the image-specific stone detail information of the arranged tomography image (S320); and determining whether the image-specific stone detail information is for the same stone by comparing the coordinates extracted from the image-specific stone detail information of the arranged tomography image with coordinates of an adjacent tomography image (S330).

In the present invention, the image-specific stone detail information of each of the tomography images may be clustered as described above to process information by aggregating the image-specific stone detail information in each of a plurality of tomography images where one urinary stone is photographed. As described above, since information on the stone in each of the tomography images for one urinary stone is collected and processed, various information on the urinary stone may be obtained.

FIG. 8 shows a plurality of tomography images img001 to img006 for analyzing the urinary stone according to one embodiment of the present invention. The images may be set with mutually different tomography heights (z-axis coordinates) as shown in FIG. 3, and may be arranged and numbered in an order of the tomography heights. As described above, since the tomography images are arranged according to the tomography heights (S310), the clustering of the image-specific stone detail information in the tomography images may be prepared.

Referring to a first tomography image img001, a urinary stone is detected at a location a by the first machine learning model and displayed as a stone region. For the stone region, a region actually corresponding to the stone may be extracted through the step S200 of extracting the image-specific stone detail information. Coordinates of the stone region extracted as described above may be extracted and stored (S320).

In this case, the urinary stone at the location a may be designated as a first urinary stone, and the image-specific stone detail information at the location a may be clustered as the first urinary stone (S330).

Referring to a second tomography image img002, the urinary stone is detected at a location b by the first machine learning model and displayed as a stone region. Similar to a case of img001, coordinates of the stone region as described above may be extracted and stored (S320).

In this case, since a difference between the coordinates of the urinary stone at the location b and the coordinates of the urinary stone at the location a of the adjacent tomography image img001 is very small, the urinary stone at the location b may be determined as a stone region for the same urinary stone. Therefore, the image-specific stone detail information at the location b may be clustered as the first urinary stone, which is the same as in the image-specific stone detail information at the location a (S330).

Accordingly, a criterion for determining whether the image-specific stone detail information is for the same stone by comparing the coordinates of the tomography images with each other may be required. In one embodiment of the present invention, in a case where a distance between the coordinates is less than or equal to a preset reference when starting points of the coordinates of the image-specific stone detail information are compared with each other, the image-specific stone detail information may be determined to be for the same stone. Alternatively, in another embodiment, coordinates of each pixel of the image-specific stone detail information may be extracted, and the image-specific stone detail information may be determined to be for the same stone when a ratio of pixels overlapping each other or the number of pixels is greater than or equal to a preset reference. As described above, in the present invention, the image-specific stone detail information may be determined to be for the same stone by processing or treating the coordinates of the image-specific stone detail information in various schemes and comparing the processed or treated coordinates with coordinates of image-specific stone detail information of the adjacent tomography image.

Referring to a third tomography image img003, the urinary stone is detected at locations c and d by the first machine learning model and displayed as a stone region. Similar to the case of img001, coordinates of the stone region as described above may be extracted and stored (S320).

In this case, since a difference between the coordinates of the urinary stone at the location d and the coordinates of the urinary stone at the location b of the adjacent tomography image img002 is very small, the urinary stone at the location d may be determined as a stone region for the same urinary stone. Therefore, the image-specific stone detail information at the location d may be clustered as the first urinary stone, which is the same as in the image-specific stone detail information at the location b.

Meanwhile, since a difference between the coordinates of the urinary stone at the location c and the coordinates of the urinary stone at the location b of the adjacent tomography image img002 is large, the urinary stone at the location c may be determined as a stone region for a new urinary stone. Therefore, the urinary stone at the location c may be designated as a second urinary stone, and the image-specific stone detail information at the location c may be clustered as the second urinary stone (S330).

Referring to a fourth tomography image img004, the urinary stone is detected at a location e by the first machine learning model and displayed as a stone region. Similar to the case of img001, coordinates of the stone region as described above may be extracted and stored (S320).

In this case, since a difference between the coordinates of the urinary stone at the location e and the coordinates of the urinary stone at the location c of the adjacent tomography image img003 is very small, the urinary stone at the location e may be determined as a stone region for the same urinary stone. Therefore, the image-specific stone detail information at the location e may be clustered as the second urinary stone, which is the same as in the image-specific stone detail information at the location c (S330).

Referring to a fifth tomography image img005, the urinary stone is detected at a location f by the first machine learning model and displayed as a stone region. Similar to the case of img001, coordinates of the stone region as described above may be extracted and stored (S320).

In this case, since a difference between the coordinates of the urinary stone at the location f and the coordinates of the urinary stone at the location e of the adjacent tomography image img003 is large, the urinary stone at the location f may be determined as a stone region for a new urinary stone. Therefore, the urinary stone at the location f may be designated as a third urinary stone, and the image-specific stone detail information at the location f may be clustered as the third urinary stone (S330).

Referring to a sixth tomography image img006, the urinary stone is detected at a location g by the first machine learning model and displayed as a stone region. Similar to the case of img001, coordinates of the stone region as described above may be extracted and stored (S320).

In this case, since a difference between the coordinates of the urinary stone at the location g and the coordinates of the urinary stone at the location f of the adjacent tomography image img005 is very small, the urinary stone at the location g may be determined as a stone region for the same urinary stone. Therefore, the image-specific stone detail information at the location g may be clustered as the third urinary stone, which is the same as in the image-specific stone detail information at the location f (S330).

In FIG. 8, the image-specific stone detail information of the stone region detected in adjacent six tomography images are clustered into three urinary stones through the above process. As a result, the image-specific stone detail information at the locations a, b, and d is clustered in the first urinary stone, the image-specific stone detail information at the locations c and e is clustered in the second urinary stone, and the image-specific stone detail information at the locations f and g is clustered in the third urinary stone. Since a plurality of pieces of image-specific stone detail information for one urinary stone are clustered as described above, in the present invention, various stone detail information for the urinary stone may be extracted by aggregating the plurality of pieces of image-specific stone detail information (S400).

In one embodiment of the present invention, the stone-specific detail information may include coordinates of the stone, a maximum sectional area of the stone, a volume of the stone, and a length of a major axis of the stone. As described above, in one embodiment of the present invention, since various information on the urinary stone are extracted and deduced from the tomography images to provide the various information to the medical staff, it is possible to assist the medical staff in making a decision for treating the urinary stone.

Figure 9:
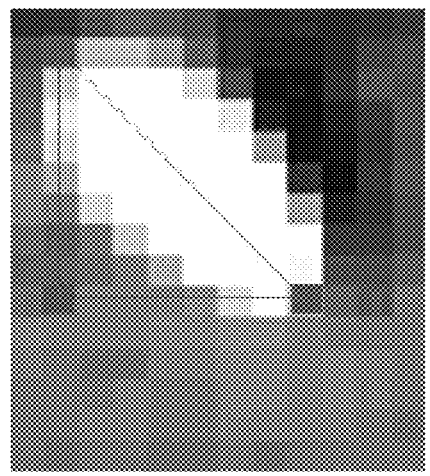
FIG. 9 is a view schematically showing a scheme of extracting a length of a major axis among stone-specific detail information according to one embodiment of the present invention.
Figure 10A:
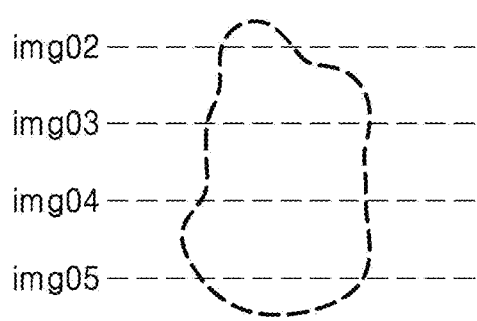
FIG. 10A is a view schematically showing a first step of extracting a volume of the stone among the stone-specific detail information according to one embodiment of the present invention.
Figure 10B:
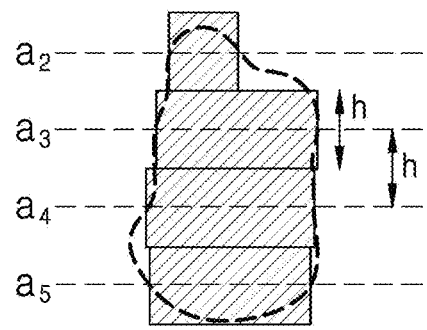
FIG. 10B is a view schematically showing a second step of extracting a volume of the stone among the stone-specific detail information according to one embodiment of the present invention.
Figure 10C:
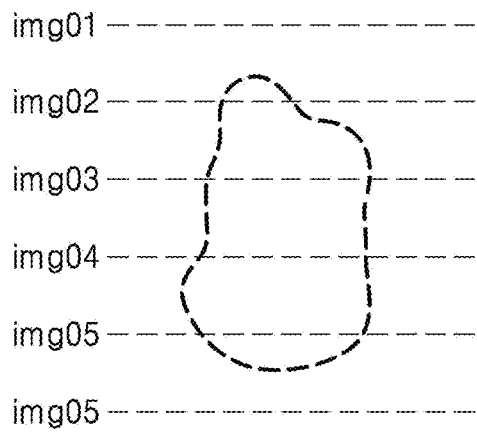
FIG. 10C is a view schematically showing a first step of extracting a volume of the stone among the stone-specific detail information according to another embodiment of the present invention.
Figure 10D:
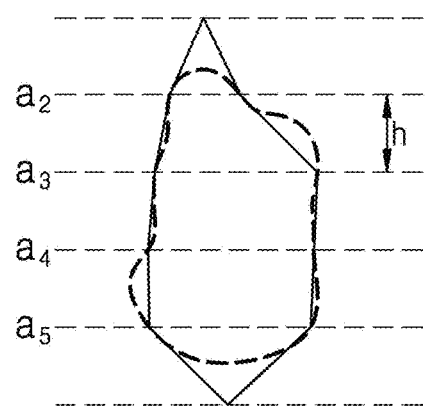
FIG. 10D is a view schematically showing a second step of extracting a volume of the stone among the stone-specific detail information according to another embodiment of the present invention.

FIG. 9 is a view schematically showing a scheme of extracting a length of a major axis among stone-specific detail information according to one embodiment of the present invention.

Referring to FIG. 9, the urinary stone is shown in white in the tomography image according to one embodiment of the present invention. The urinary stone may have a sectional shape elongated to one side as shown in FIG. 9, or may have a round sectional shape as a whole. In this case, when the urinary stone has the sectional shape elongated to one side, a length of a major axis of the elongated sectional shape may be main information of the urinary stone. This is because it is necessary to determine whether the urinary stone can be naturally discharged or not when determining whether to perform the surgery for the urinary stone, and the urinary stone is difficult to be discharged through a ureter or the like when the urinary stone has the sectional shape elongated to one side as compared with a case where the urinary stone has the round sectional shape as a whole.

An auxiliary line for extracting the length of the major axis of the urinary stone having the shape elongated to one side as described above is shown in FIG. 9. In one embodiment of the present invention, two points (an upper left end and a lower right end in FIG. 9) that most protrude from the urinary stone may be extracted, and a length of a line segment connecting the two points may be the length of the major axis. In this case, a right-angled triangle may be formed through an auxiliary point as indicated in a lower left end to extract a height (the number of vertical pixels) and a width (the number of horizontal pixels) of the right-angled triangle, and the extracted height and width may be applied to Pythagorean theorem, so that the length of the long axis (a length of a hypotenuse) may be extracted.

FIG. 10 is a view schematically showing a scheme of extracting a volume of the stone among the stone-specific detail information according to one embodiment of the present invention.

In one embodiment of the present invention, the tomography heights may be set with a preset interval, and, in the step S400 of extracting the stone-specific detail information, a volume of each stone may be extracted based on an area of the image-specific stone detail information and the interval of the tomography heights.

The clustered image-specific stone detail information may include information in each tomography image where a corresponding urinary stone is photographed. The image-specific stone detail information may include information on an area of the urinary stone in a corresponding tomography image. This may be extracted by an area of pixels determined as the urinary stone in the tomography image as described above.

In the present invention, a volume of the stone may be extracted based on the area of the urinary stone in the tomography image and the interval of the tomography heights of the tomography image as described above.

FIG. 10($a$) shows a state in which a urinary stone is photographed over a plurality of tomography images img02 to img05. The tomography images may have a difference in photographing height by a preset interval h.

Meanwhile, a sectional area of the urinary stone may be extracted from each of the tomography images as described above. In this case, an area of the urinary stone in img02 may be denoted by $a_2$, an area of the urinary stone in img03 may be denoted by $a_3$, an area of the urinary stone in img04 may be denoted by $a_4$, and an area of the urinary stone in img05 may be denoted by $a_5$.

In one embodiment of the present invention, an approximate volume of the urinary stone may be extracted by simply multiplying the area of the urinary stone in each of the tomography images by the interval of the tomography heights, and summing up multiplication results.

Referring to FIG. 10($b$), when the area $a_2$ in img02 is multiplied by the interval h of the tomography heights, a volume of an uppermost box may be obtained. Similarly, when each of the areas in img03, img04, and img05 is multiplied by the height h, a volume of a box over each of the tomography images may be obtained. When the volumes extracted as described above are summed up, the approximate volume of the urinary stone may be extracted.

Meanwhile, in another embodiment of the present invention, the volume of the stone may be extracted by cumulatively summing a value obtained by multiplying the interval of the tomography heights by an average of areas of the image-specific stone detail information of two tomography images taken at adjacent tomography heights among the tomography images including the image-specific stone detail information for the stone.

Referring to FIG. 10, descriptions will be given using img01 and img06 in which the urinary stone is not photographed as shown in FIG. 10($c$).

As described in FIGS. 10($a$) and 10($b$), the urinary stone is photographed over a plurality of tomography images img02 to img05. When the areas of the urinary stone in the tomography images are denoted by $a_2$, $a_3$, $a_4$, and $a_5$, respectively, the approximate volume of the urinary stone may be extracted as shown in FIG. 10($d$). In FIG. 10($d$), a volume of an uppermost box indicated by a triangle between img01 and img02 may be approximated as an average $((0+a_2)/2)$ of an area (0) of the urinary stone in img01 and the area $a_2$ of the urinary stone in img02. Similarly, a volume of a box indicated by a rectangle between img02 and img03 may be approximated as an average $((a_2+a_3)/2)$ of the area $a_2$ of the urinary stone in img02 and the area $a_3$ of the urinary stone in img03; a volume of a box indicated by a rectangle between img03 and img04 may be approximated as an average $((a_3+a_4)/2)$ of the area $a_3$ of the urinary stone in img03 and the area $a_4$ of the urinary stone in img04; a volume of a box indicated by a rectangle between img04 and img05 may be approximated as an average $((a_4+a_5)/2)$ of the area $a_4$ of the urinary stone in img04 and the area as of the urinary stone in img05; and a volume of a box indicated by a triangle between img05 and img06 may be approximated by an average $((a_5+0)/2)$ of the area as of the urinary stone in img05 and an area (0) of the urinary stone in img06. When all the volumes of the boxes approximated as described above are summed up, the approximate volume of the urinary stone as shown in the drawing may be obtained.

As described above, in one embodiment of the present invention, the volume of the stone may be extracted based on the areas of the urinary stone in the tomography images and the interval of the tomography heights of the tomography images, and the volume of the stone extracted as described above may be used as data for allowing the medical staff to make a decision for the treatment of the stone.

Figure 11:
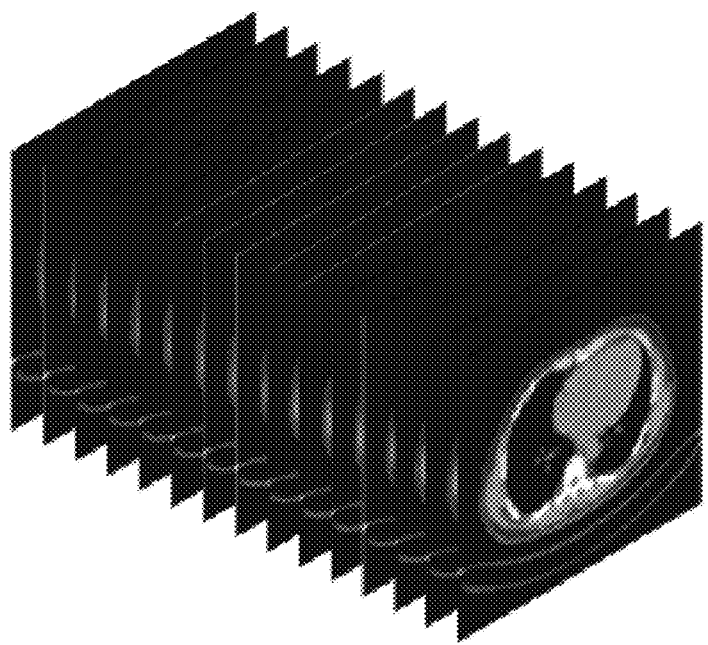
FIG. 11 is a view schematically showing a state in which a three-dimensional (3D) body model is generated in order to display the urinary stone information according to one embodiment of the present invention.

Although two embodiments of the present invention for extracting the volume of the stone as shown in FIG. 10 have been described, the present invention is not limited thereto, and the volume of the urinary stone may be extracted in various schemes by using the areas of the urinary stone in the tomography images and the interval of the tomography heights. FIG. 11 is a view schematically showing a state in which a three-dimensional (3D) body model is generated in order to display the urinary stone information according to one embodiment of the present invention, and FIG. 12 is a view schematically showing a state in which the urinary stone information is displayed on the generated 3D body model according to one embodiment of the present invention.

In one embodiment of the present invention, in the step S700 of displaying the urinary stone information, the extracted urinary stone information may be displayed by overlaying the extracted urinary stone information on a three-dimensional (3D) body model generated based on the tomography images In the present invention, detailed information on the urinary stone may be displayed to the medical staff attempts to treat the urinary stone through the step S700 of displaying the urinary stone information, so that the medical staff may clearly recognize the information on the urinary stone. To this end, in one embodiment of the present invention, since the 3D body model of the patient is generated based on the tomography images, and the urinary stone information is displayed on the 3D body model, the medical staff may recognize information such as the location and the size of the urinary stone.

As described above in FIG. 3, the tomography images may have mutually different tomography heights in the height direction (z-axis direction) of the patient 10. Therefore, as shown in FIG. 11, the tomography images may be arranged and composed according to the tomography heights to perform modeling, so that the 3D body model of the patient may be generated. The 3D body model generated as described above may include various body organs and an object such as a urinary stone displayed in the tomography image.

Figure 12A:
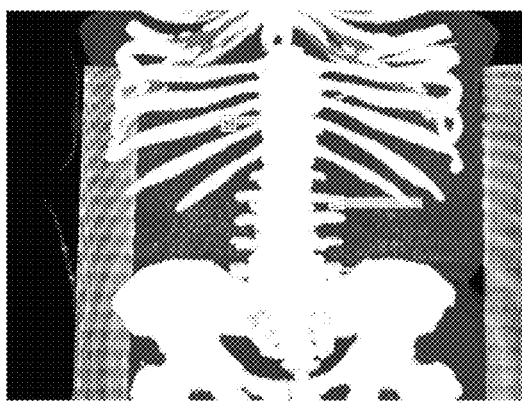
FIG. 12A shows the 3D body model viewed from the abdomen of the patient.

Referring to FIG. 12, FIG. 12(a) shows the 3D body model viewed from abdomen of the patient. One urinary stone is displayed in each of an upper left end and a center of the drawing as a red region, and the stone-specific detail information such as a size of each urinary stone is labeled and displayed. As described above, in one embodiment of the present invention, since the extracted urinary stone information is displayed by overlaying the extracted urinary stone information on the 3D body model such that the stone-specific detail information may be recognized together with the location of the urinary stone, the medical staff may easily recognize the urinary stone information and use the urinary stone information to proceed with the treatment of the patient.

Meanwhile, in one embodiment of the present invention, in the step S700 of displaying the urinary stone information, a display angle and a size of the 3D body model may be adjustable according to an input of the user. This is to allow the medical staff to easily recognize the location, the size, and the like of the urinary stone by rotating and enlarging/reducing the 3D body model.

FIG. 12(a) shows the 3D body model viewed from the abdomen of the patient as described above. Accordingly, the location of the urinary stone indicated by the red region in the 3D body model and the stone-specific detail information for each urinary stone may be recognized.

However, when the location of the urinary stone is recognized in one direction as described above, it may be difficult to determine an accurate location of the urinary stone. Although the urinary stone located at the upper left end of the drawing may be recognized to be present at a location corresponding to ribs through FIG. 12(a), a depth at which the urinary stone is located may not be recognized.

Figure 12B:
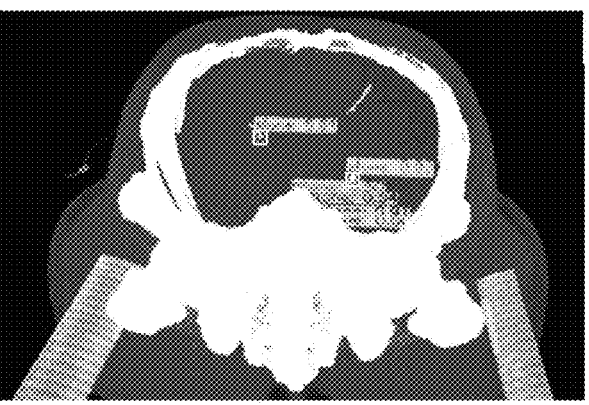
FIG. 12B shows the 3D body model viewed from a leg of the patient.

Therefore, in one embodiment of the present invention, since the 3D body model is rotated as shown in FIG. 12(b) to observe the 3D body model from a leg of the patient, the depth at which the urinary stone is located may be recognized.

In addition, since the 3D body model is rotated and enlarged/reduced, a urinary stone that is covered with body organs such as vertebrae and pelvic bones of the patient so as not to be observed may be recognized as shown in FIG. 12(b).

FIG. 13 is a view schematically showing a configuration of an apparatus for providing urinary stone information according to one embodiment of the present invention.

According to one embodiment of the present invention, an apparatus for providing urinary stone information may include: a stone region information extraction unit 100 for extracting at least one stone region information by using a first machine learning model trained for each of a plurality of tomography images having mutually different tomography heights; an image-specific stone detail information extraction unit 200 for extracting image-specific stone detail information related to a region actually corresponding to a stone in each stone region based on color information of a pixel in the stone region of the tomography image corresponding to the at least one stone region information; an image-specific stone detail information clustering unit 300 for clustering the image-specific stone detail information for a same stone among the image-specific stone detail information of each of the tomography images; a stone-specific detail information extraction unit 400 for extracting stone-specific detail information including a size of each stone based on information including the stone region information and the image-specific stone detail information; a urinary stone information generation unit 500 for generating or providing the urinary stone information based on at least one of the tomography image, the stone region information, the image-specific stone detail information, and the stone-specific detail information according to a request of a user; a urinary stone information display unit 600 for displaying the urinary stone information generated according to the request of the user; and a surgery success probability extraction unit 700 for extracting a success probability of surgery by using a preset condition or a second machine learning model trained based on information including the stone region information and the image-specific stone detail information for each stone.

Components of the apparatus for providing the urinary stone information may perform the steps of the method for providing the urinary stone information as described above with configurations for performing each of the steps, respectively.

Figure 13B:
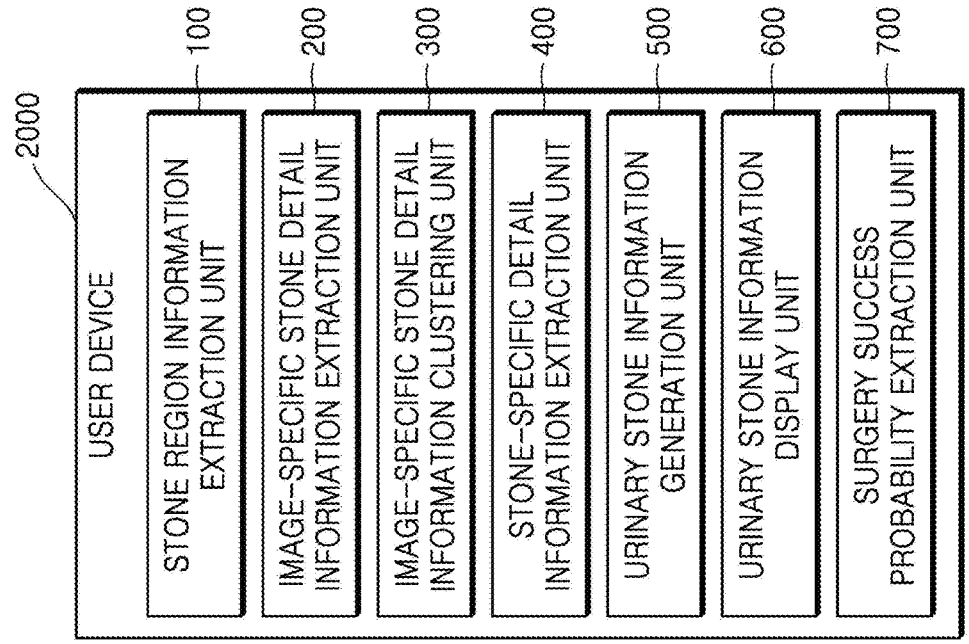
FIG. 13B is a view schematically showing a configuration of a user device apparatus for providing urinary stone information according to one embodiment of the present invention.
Figure 13A:
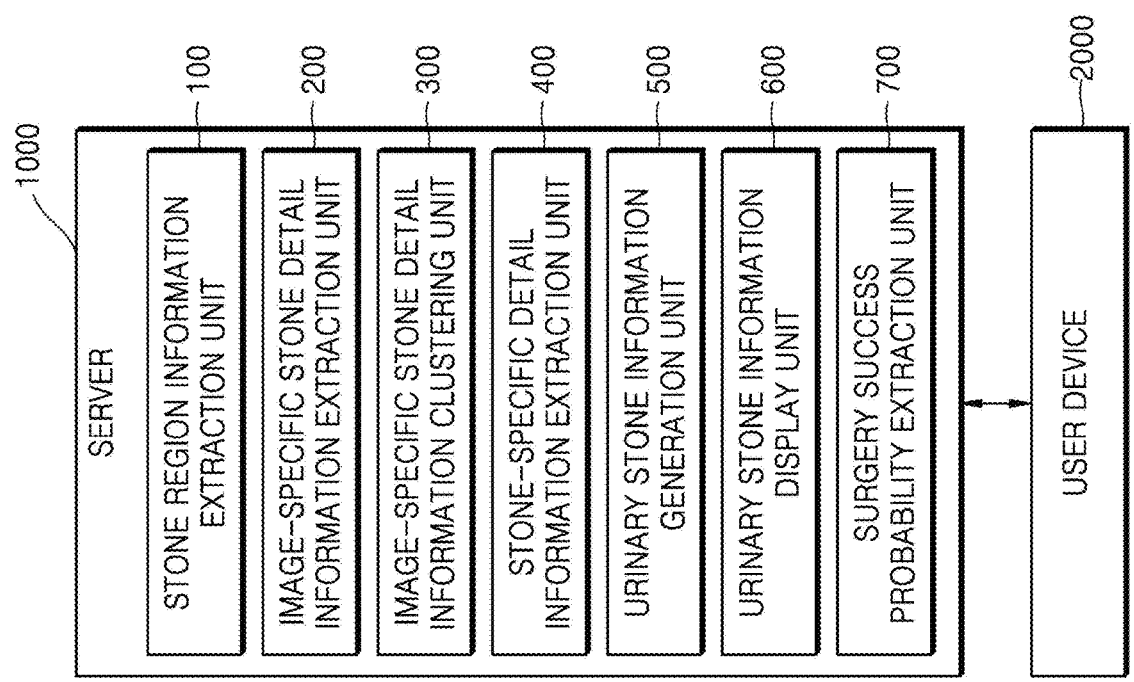
FIG. 13A is a view schematically showing a configuration of a server apparatus for providing urinary stone information according to one embodiment of the present invention.

Referring to FIG. 13(a), in one embodiment of the present invention, in a network including a server 1000 and a user terminal 2000, the server 1000 may serve as the apparatus for providing the urinary stone information, and the user terminal 2000 may access the server 1000 to upload the tomography image, so that the urinary stone information may be provided through the apparatus for providing the urinary stone information.

Meanwhile, referring to FIG. 13(b), in one embodiment of the present invention, the user terminal 2000 may serve as the apparatus for providing the urinary stone information, and the user terminal 2000 may extract the urinary stone information from the tomography image and use the extracted urinary stone information.

Alternatively, although not shown in FIG. 13, some of the components of the apparatus for providing the urinary stone information may be included in the server 1000, and some of the components of the apparatus for providing the urinary stone information may be included in the user terminal 2000 to receive the urinary stone information. For example, the server 1000 may include the urinary stone information generation unit 500 to generate the urinary stone information according to the request of the user, and the urinary stone information may be displayed to the user through the urinary stone information display unit 600 included in the user terminal 2000.

Figure 14:
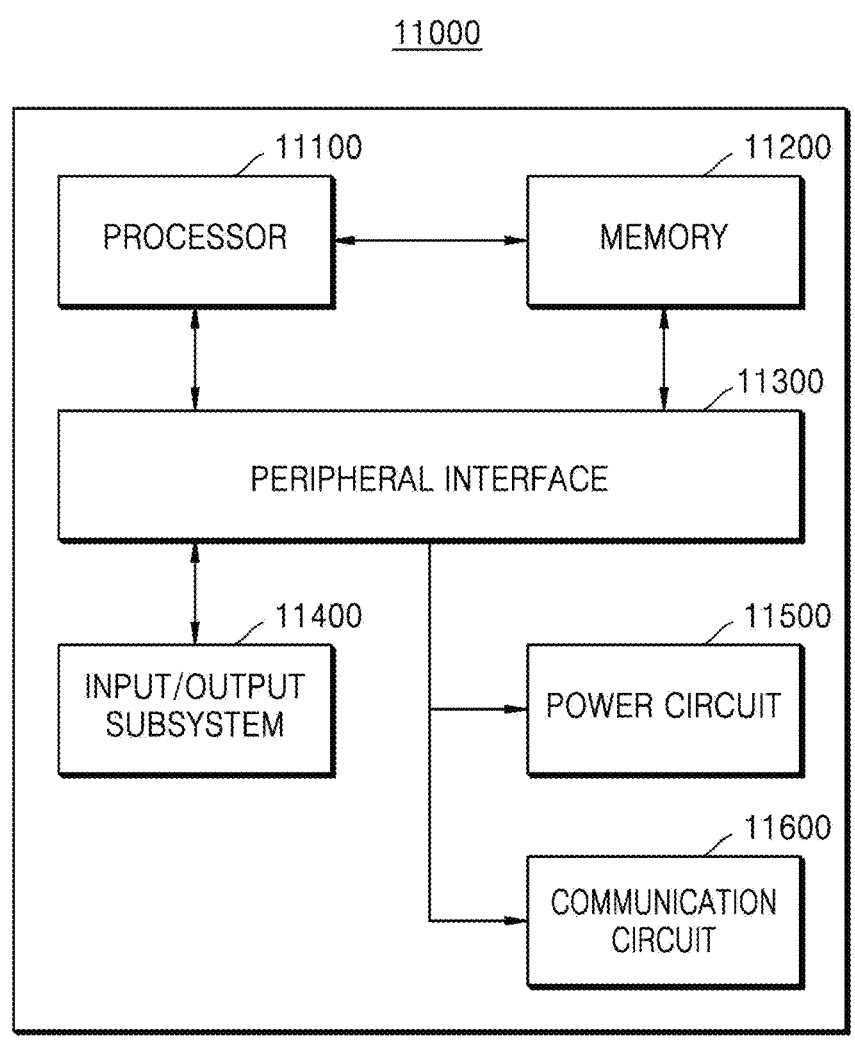
FIG. 14 is a block diagram for describing one example of an internal configuration of a computing device according to one embodiment of the present invention.

FIG. 14 is a block diagram for describing one example of an internal configuration of a computing device according to one embodiment of the present invention.

As shown in FIG. 14, a computing device 11000 may include at least one processor 11100, a memory 11200, a peripheral interface 11300, an input/output (I/O) subsystem 11400, a power circuit 11500, and a communication circuit 11600. In this case, the computing device 11000 may correspond to the apparatus for providing the urinary stone information, a server, or a client.

The memory 11200 may include, for example, a high-speed random access memory, a magnetic disk, an SRAM, a DRAM, a ROM, a flash memory, and a nonvolatile memory. The memory 11200 may include software modules, instruction sets, or various other data required for an operation of the computing device 11000.

In this case, an access to the memory 11200 from other components of the processor 11100 or the peripheral interface 11300 may be controlled by the processor 11100.

The peripheral interface 11300 may combine an input and/or output peripheral device of the computing device 11000 to the processor 11100 and the memory 11200. The processor 11100 may execute the software module or the instruction set stored in the memory 11200 to perform various functions for the computing device 11000 and process data.

The I/O subsystem 11400 may combine various input/output peripheral devices to the peripheral interface 11300. For example, the I/O subsystem 11400 may include a controller for combining the peripheral device, such as a monitor, a keyboard, a mouse, a printer, or a touch screen or sensor, if necessary, to the peripheral interface 11300. According to another aspect, the input/output peripheral devices may be combined to the peripheral interface 11300 without passing through the I/O subsystem 11400.

The power circuit 11500 may provide a power to all or some of the components of the terminal. For example, the power circuit 11500 may include a power management system, at least one power source such as a battery or an alternating current (AC), a charging system, a power failure detection circuit, a power converter or inverter, a power status indicator, and any other components for generating, managing, and distributing the power.

The communication circuit 11600 may use at least one external port to enable communication with other computing devices.

Alternatively, as described above, the communication circuit 11600 may include an RF circuit, if necessary, to transmit and receive an RF signal, also known as an electromagnetic signal, thereby enabling the communication with other computing devices.

The above embodiment of FIG. 14 is merely an example of the computing device 11000. In the computing device 11000, some components shown in FIG. 14 may be omitted, additional components not shown in FIG. 14 may be further provided, or a configuration or arrangement for combining at least two components may be provided. For example, a computing device for a communication terminal in a mobile environment may further include a touch screen, a sensor, and the like in addition to the components shown in FIG. 14, and the communication circuit 11600 may include a circuit for RF communication in various communication schemes (such as WiFi, 3G, LTE, Bluetooth, NFC, and Zigbee). The components that may be included in the computing device 11000 may be implemented as hardware, software, or a combination of both hardware and software including at least one integrated circuit specialized in signal processing or an application.

The methods according to the embodiments of the present invention may be implemented in the form of program instructions that may be executed through various computing devices, and may be recorded in a computer-readable medium. Particularly, a program according to the present embodiment may be configured as a PC-based program or an application dedicated to a mobile terminal. The application to which the present invention is applied may be installed in the user terminal through a file provided by a file distribution system. For example, the file distribution system may include a file transmission unit (not shown) for transmitting the file according to a request of the user terminal.

According to one embodiment of the present invention, a urinary stone can be automatically detected from a tomography image by using a machine learning model.

According to one embodiment of the present invention, the urinary stone can be detected very rapidly by detecting the urinary stone based on a YOLO artificial neural network algorithm.

According to one embodiment of the present invention, information including a size and a location of the detected urinary stone can be automatically extracted.

According to one embodiment of the present invention, a volume of the urinary stone can be extracted based on an area of the urinary stone in the tomography image.

According to one embodiment of the present invention, an appropriate treatment scheme can be selected by extracting a success probability of urinary stone surgery by using the machine learning model.

According to one embodiment of the present invention, urinary stone information can be clearly recognized by displaying the urinary stone information on a 3D body model.

Although the above embodiments have been described by the specific embodiments and drawings, various changes and modifications can be made by those skilled in the art from the above description. For example, even when the described techniques are performed in an order different from the described manner, or the described components such as a system, a structure, a device, and a circuit are coupled or combined in a form different from the described manner, or replaced or substituted by other components or equivalents, appropriate results may be achieved. Therefore, other implementations, other embodiments, and equivalents to the claims are also within the scope of the appended claims.

What is claimed is:

1. A method for providing urinary stone information, which is performed in a computing system having at least one processor and at least one memory, the method comprising:
   extracting at least one stone region information by using a first machine learning model trained for each of a plurality of tomography images having mutually different tomography heights;
   extracting image-specific stone detail information related to a region actually corresponding to a stone in each stone region based on color information of a pixel in the stone region of the tomography image corresponding to the at least one stone region information;
   clustering the image-specific stone detail information for a same stone among the image-specific stone detail information of each of the tomography images;
   extracting stone-specific detail information including a size of each stone based on information including the stone region information and the image-specific stone detail information; and
   generating or providing the urinary stone information based on at least one of the tomography image, the stone region information, the image-specific stone detail information, and the stone-specific detail information according to a request of a user.

2. The method of claim 1, wherein the tomography heights are set with a preset interval, and
   in the extracting of the stone-specific detail information, a volume of each stone is extracted based on an area of the image-specific stone detail information and the interval of the tomography heights.

3. The method of claim 2, wherein the volume of the stone is extracted by cumulatively summing a value obtained by multiplying the interval of the tomography heights by an average of areas of the image-specific stone detail information of two tomography images taken at adjacent tomography heights among the tomography images including the image-specific stone detail information for the stone.

4. The method of claim 1, wherein the clustering of the image-specific stone detail information includes:
   arranging the tomography images according to the tomography heights;
   extracting coordinates of the image-specific stone detail information of the arranged tomography image; and
   determining whether the image-specific stone detail information is for the same stone by comparing the coordinates extracted from the image-specific stone detail information of the arranged tomography image with coordinates of an adjacent tomography image.

5. The method of claim 1, wherein the stone-specific detail information includes coordinates of the stone and a volume of the stone.

6. The method of claim 1, further comprising displaying the urinary stone information generated according to the request of the user,
   wherein, in the displaying of the urinary stone information, the extracted urinary stone information is displayed by overlaying the extracted urinary stone information on a three-dimensional (3D) body model generated based on the tomography images.

7. The method of claim 6, wherein, in the displaying of the urinary stone information, a display angle and a size of the 3D body model is adjustable according to an input of the user.

8. The method of claim 1, further comprising extracting a success probability of extracorporeal shock wave lithotripsy by using a preset condition or a second machine learning model trained based on information including the stone region information and the image-specific stone detail information for each stone.

9. A non-transitory computer-readable medium recorded with a program for performing the method for providing the urinary stone information according to one of claims 1 to 8.

10. An apparatus for providing urinary stone information, the apparatus comprising:
    a stone region information extraction unit for extracting at least one stone region information by using a first machine learning model trained for each of a plurality of tomography images having mutually different tomography heights;
    an image-specific stone detail information extraction unit for extracting image-specific stone detail information related to a region actually corresponding to a stone in each stone region based on color information of a pixel in the stone region of the tomography image corresponding to the at least one stone region information;
    an image-specific stone detail information clustering unit for clustering the image-specific stone detail information for a same stone among the image-specific stone detail information of each of the tomography images;
    a stone-specific detail information extraction unit for extracting stone-specific detail information including a size of each stone based on information including the stone region information and the image-specific stone detail information; and
    a urinary stone information generation unit for generating or providing the urinary stone information based on at least one of the tomography image, the stone region information, the image-specific stone detail information, and the stone-specific detail information according to a request of a user.

* * * * *